(12) United States Patent
Peng et al.

(10) Patent No.: US 11,073,503 B2
(45) Date of Patent: Jul. 27, 2021

(54) AREA MONITORING DEVICE, AND METHOD OF OPERATING SAME

(71) Applicant: Molex, LLC, Lisle, IL (US)

(72) Inventors: Wenfeng Peng, North Aurora, IL (US); Alexander S. Chernyshov, Naperville, IL (US)

(73) Assignee: Molex, LLC, Lisle, IL (US)

(*) Notice: Subject to any disclaimer, the term of this patent is extended or adjusted under 35 U.S.C. 154(b) by 132 days.

(21) Appl. No.: 16/040,657

(22) Filed: Jul. 20, 2018

(65) Prior Publication Data

US 2019/0025264 A1    Jan. 24, 2019

Related U.S. Application Data

(60) Provisional application No. 62/535,412, filed on Jul. 21, 2017.

(51) Int. Cl.
*G01N 30/54* (2006.01)
*G01N 33/00* (2006.01)
*B01D 53/04* (2006.01)
*G01N 30/02* (2006.01)
*B01D 53/30* (2006.01)

(52) U.S. Cl.
CPC ......... *G01N 30/54* (2013.01); *G01N 33/0047* (2013.01); *B01D 53/04* (2013.01); *B01D 53/0438* (2013.01); *B01D 53/30* (2013.01); *B01D 2253/102* (2013.01); *B01D 2257/708* (2013.01); *B01D 2259/45* (2013.01); *G01N 2030/025* (2013.01)

(58) Field of Classification Search
CPC ... G01N 1/24; G01N 1/2214; G01N 2001/245
See application file for complete search history.

(56) References Cited

U.S. PATENT DOCUMENTS

| | | | |
|---|---|---|---|
| 2006/0102844 A1* | 5/2006 | Sauer | G01N 21/3504 250/339.13 |
| 2007/0029477 A1* | 2/2007 | Miller | G01N 27/624 250/290 |
| 2012/0024042 A1* | 2/2012 | Vass | G01N 33/0031 73/23.34 |
| 2012/0270334 A1* | 10/2012 | Ojeda | G01N 1/405 436/178 |

* cited by examiner

*Primary Examiner* — Alexander A Mercado

(57) ABSTRACT

An area monitoring device is placed in a location to monitor volatile organic compounds emissions. The device includes a gas sensor capable of detecting VOCs, a sorbent material capable of absorbing VOC molecules, and a heating element positioned in close relation to, or in direct contact with, the sorbent material. After a period of time during which the sorbent material absorbs VOC molecules, the sorbent material is heated to cause the sorbent material to release a gas containing VOC molecules. The amount of released VOC molecules is sensed and calculated. Data is compiled and analyzed. This is accomplished without removing the device from the location. A pump may be provided to force ambient air through the device.

4 Claims, 7 Drawing Sheets

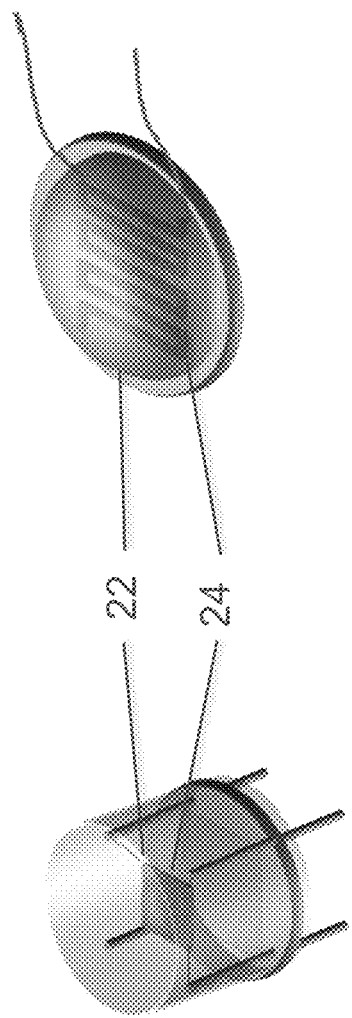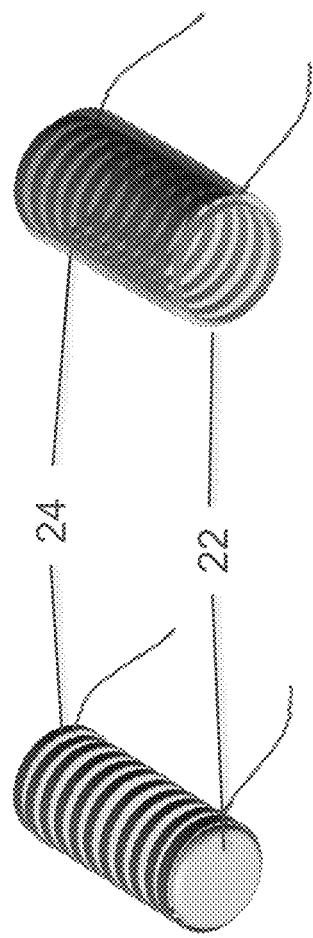

AREA MONITORING DEVICE, AND METHOD OF OPERATING SAME

RELATED APPLICATIONS

This application claims priority to U.S. Provisional Application Ser. No. 62/535,412, filed on Jul. 21, 2017.

TECHNICAL FIELD

This disclosure relates to the field of sensors, more specifically to the field of area monitoring sensors and the method of operating same.

DESCRIPTION OF RELATED ART

Process plants, such as petroleum refineries and chemical manufacturing facilities, have many complex issues associated with gas leaks. In October 2007, the United States Environmental Protection Agency ("EPA") issued a document entitled "Leak Detection and Repair—A Best Practices Guide". According to this document, the EPA has determined that leaking equipment, such as valves, pumps, and connectors, are the largest source of emissions of gases, such as volatile organic compounds ("VOCs") and volatile hazardous air pollutants ("VHAPs"), from petroleum refineries and chemical manufacturing facilities.

VOCs contribute to the formation of ground-level ozone. Ozone is a major component of smog and may cause or aggravate respiratory disease. Many areas of the United States do not meet the National Ambient Air Quality Standard ("NAAQS") for ozone.

Some species of VOCs are also classified as VHAPs. Some common VHAPs emitted from refineries and chemical plants include acetaldehyde, benzene, formaldehyde, methylene chloride, naphthalene, toluene, and xylene.

A typical refinery or chemical plant can emit hundreds of tons per year of VOCs from leaking equipment, such as valves, connectors, pumps, sampling connections, compressors, pressure-relief devices, and open-ended lines.

Thus, detecting gas leaks in process plants has been a huge challenge. Gas quickly disperses in air, such that the concentration of gas decreases exponentially from the leak point. At a fixed point, gas comes and goes due to constant wind. Trucks or maintenance activities can cause spikes in VOC. Many field devices do not provide meaningful readings below a few parts per million ("ppm"). Existing sensor technologies are either not sensitive enough or are not suitable for continuous operation in the open air where weather conditions affect sensor readings, especially at low gas concentrations.

To minimize the emission of VOCs, the EPA has adopted two different methods for implementation by process plants. EPA Method 21 requires trained technicians to manually check leaks at each component within a process plant at specified, regular intervals to determine whether it is leaking. However, as a typical process plant will have hundreds of thousands of components that must be checked, the work associated with EPA Method 21 is extremely inefficient, costly, and unreliable. Further information regarding EPA Method 21 can be found at https://www3.epa.gov/ttnemc01/promgate/m-21.pdf and https://www.epa.gov/emc/method-21-volatile-organic-compound-leaks which information is hereby incorporated by reference. EPA Method 325A/B specifies a passive monitoring method where sampling tubes are placed along fence lines for a fixed period of time and are then collected by a technician and mailed to an independent lab for analysis. EPA Method 325A/B is also costly and time consuming and, furthermore, does not provide any indication to the process plant as to where any leaks may be occurring. Further information regarding EPA Method 325A/B can be found at https://www3.epa.gov/ttnemc01/promgate/m-325a.pdf which information is hereby incorporated by reference.

As a result of the foregoing, certain individuals would appreciate further improvements in Leak Detection and Repair programs, including the use of area monitoring sensors and devices, and systems utilizing same.

SUMMARY

An area monitoring device is placed in a location to monitor volatile organic compounds (VOCs) emissions. The area monitoring device includes a gas sensor capable of detecting VOCs, a sorbent material capable of absorbing volatile organic compound (VOC) molecules, and a heating element positioned in close relation to, or which may directly contact, the sorbent material. After a period of time during which the sorbent material absorbs VOC molecules, the sorbent material is heated to cause the sorbent material to release a gas containing VOC molecules. The amount of released VOC molecules is sensed and calculated. Data is compiled and analyzed. This is accomplished without removing the area monitoring device from the location. A pump may be provided to force ambient air through the device and therefore accelerate the process.

This summary is provided merely for purposes of summarizing some example embodiments so as to provide a basic understanding of some aspects of the disclosure. Accordingly, it will be appreciated that the above described example embodiments are merely examples and should not be construed to narrow the scope or spirit of the disclosure in any way. Other embodiments, aspects, and advantages of various disclosed embodiments will become apparent from the following detailed description taken in conjunction with the accompanying drawings which illustrate, by way of example, the principles of the described embodiments.

BRIEF DESCRIPTION OF THE DRAWINGS

FIGS. 3A-3D show example heating elements and sorbent materials that may be used in the area monitoring device;

DETAILED DESCRIPTION

Figure 1:
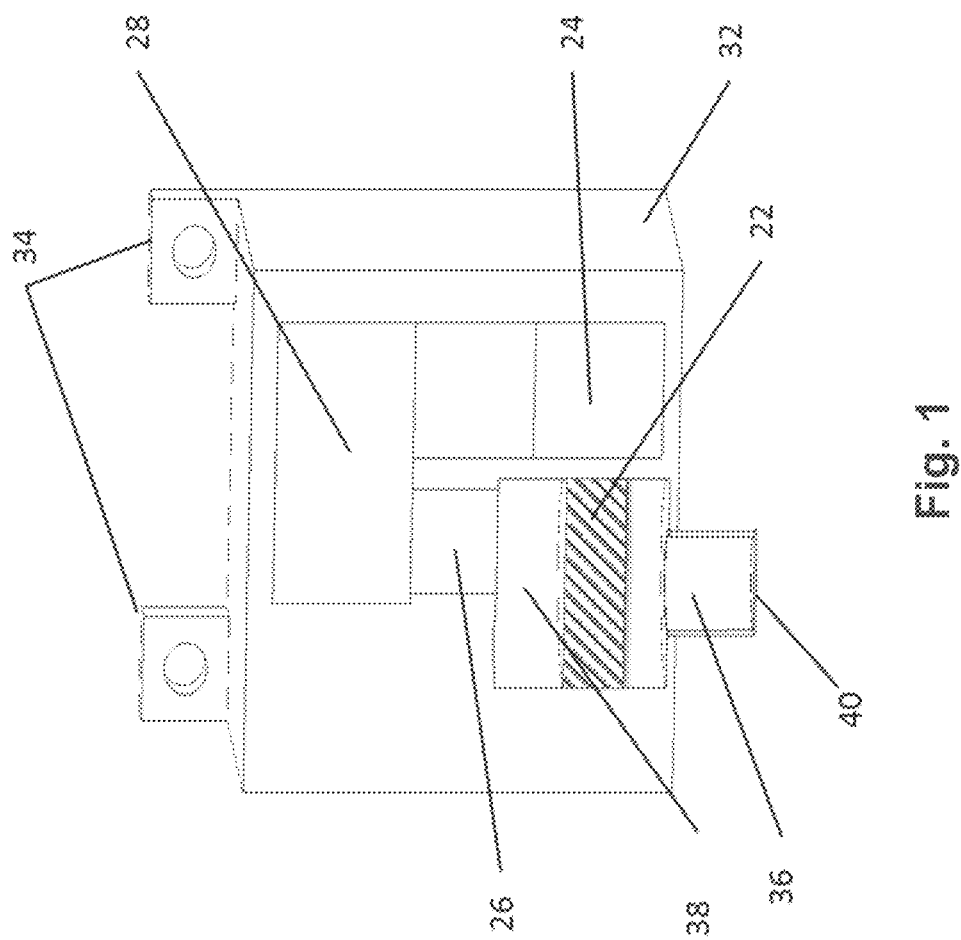
FIG. 1 is a cross-sectional view of an area monitoring device in a location in accordance with a first embodiment of the disclosure.

While the disclosure may be susceptible to embodiment in different forms, there is shown in the drawings, and herein will be described in detail, specific embodiments with the understanding that the present disclosure is to be considered an exemplification of the principles of the disclosure and is not intended to limit the disclosure to that as illustrated and described herein. Therefore, unless otherwise noted, features disclosed herein may be combined to form additional combinations that were not otherwise shown for purposes of brevity. It will be further appreciated that in some embodiments, one or more elements illustrated by way of example in a drawing(s) may be eliminated and/or substituted with alternative elements within the scope of the disclosure.

Figure 2:
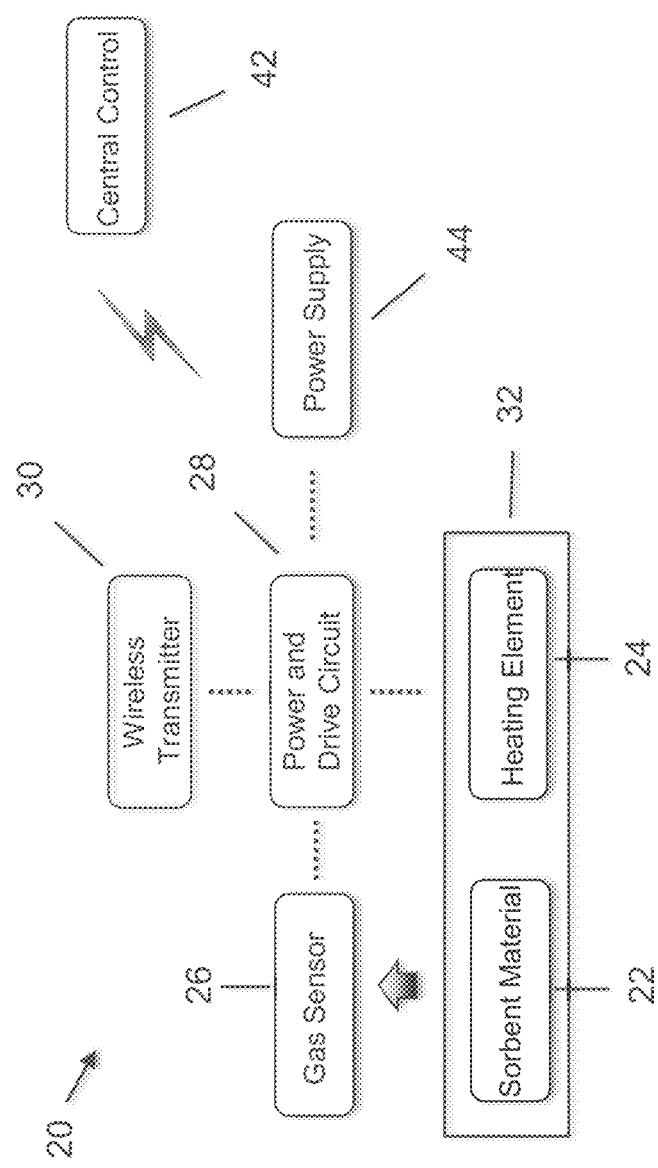
FIG. 2 is a schematic diagram of the area monitoring device of FIG. 1 and showing a central control.

A first embodiment of an area monitoring device 20 is illustrated in FIGS. 1 and 2. The area monitoring device 20 includes a passive sorbent material 22, a heating element 24, a gas sensor 26, a power and drive circuit 28, and a wireless transmitter 30. The passive sorbent material 22 is positioned in close relation to, or may directly contact, the heating element 24. The heating element 24 is operatively connected to the power and drive circuit 28. The power and drive circuit 28 is further operatively connected to the gas sensor 26 and to the wireless transmitter 30. The gas sensor 26 is positioned proximate to the sorbent material 22. The sorbent material 22 and the heating element 24 may be provided in or on a housing 32. The gas sensor 26, the power and drive circuit 28 and the wireless transmitter 30 may also be provided in or on the housing 32 or may be separated from the housing 32.

The sorbent material 22 is a material that is suitable for absorbing volatile organic compound (VOC) molecules in air over time at low concentration of VOC molecules. The sorbent material 22 could be of a number of varieties, including a charcoal filler, various powders, textiles, paints (e.g., mixed with polymers), etc. The sorbent material 22 may also be thin-film deposited, if desired. The higher the gas concentration, the more VOC molecules the passive sorbent material 22 collects. Furthermore, the longer the time, the more VOC molecules the passive sorbent material 22 collects.

The heating element 24 is used to heat the sorbent material 22 to a temperature where the VOC molecules absorbed in the sorbent material 22 are released as a gas from the sorbent material 22. The heating element 24 could be of a number of varieties such as a micro-electro-mechanical (MEMS) heater as illustrated in FIG. 3A where the sorbent material 22 is generally wrapped around the MEMS heater, a planar heater as illustrated in FIG. 3B where the sorbent material 22 is provided above the planar heater, and a coil heater as illustrated in FIGS. 3C and 3D where the sorbent material 22 is provided inside the coil heater (FIG. 3C) or where the sorbent material 22 is provided outside of, and on the ends, of the coil heater (FIG. 3D). There are also other ways of generating thermal energy to release gas molecules from the sorbet material 22 such as, but not limited to, electromagnetic energy such as a lamp, microwave and inductive heating and, as, such, such examples are considered to be included in the definition of the heating element 24.

The gas sensor 26 is a sensor that is suitable to sense volatile organic compounds (VOCs) and to measure the amount of VOC molecules present in an area 34. The gas sensor 26 could be of a number of varieties, including, but not limited to, photoionization detectors (PIDs), metal oxide semiconductor (MOS) and other chemi-resistor sensors, non-dispersive infrared (NDIR) sensors, photoacoustic sensors (PAS) and electro-chemical sensors. The gas sensor 26 may include a heat protector in order to protect the gas sensor 26 from the heat emitted from the heating element 24.

The housing 32 of the area monitoring device 20 may have any suitable configuration. The area monitoring device 20 may be held in its desired position by any appropriate means 34, such as for example a bracket structure (as shown), such that it is suitably attached to a structure in the desired location where it is to monitor. The housing 32 may have an inlet 36 which opens to a chamber 38 within the housing 32 in which the sorbent material 22 and the heating element 24 are preferably seated. The gas sensor 26, the power and drive circuit 28 and the wireless transmitter 30 may also be provided in the chamber 38. The housing 32 serves to protect the sorbent material 22 and the heating element 24 from the elements. The inlet 36 may be outfitted with a protective membrane 40 which will allow gases to enter the chamber 38, but which will prevent undesired materials, such as water, dust and dirt, from entering the chamber 38.

Figure 4:
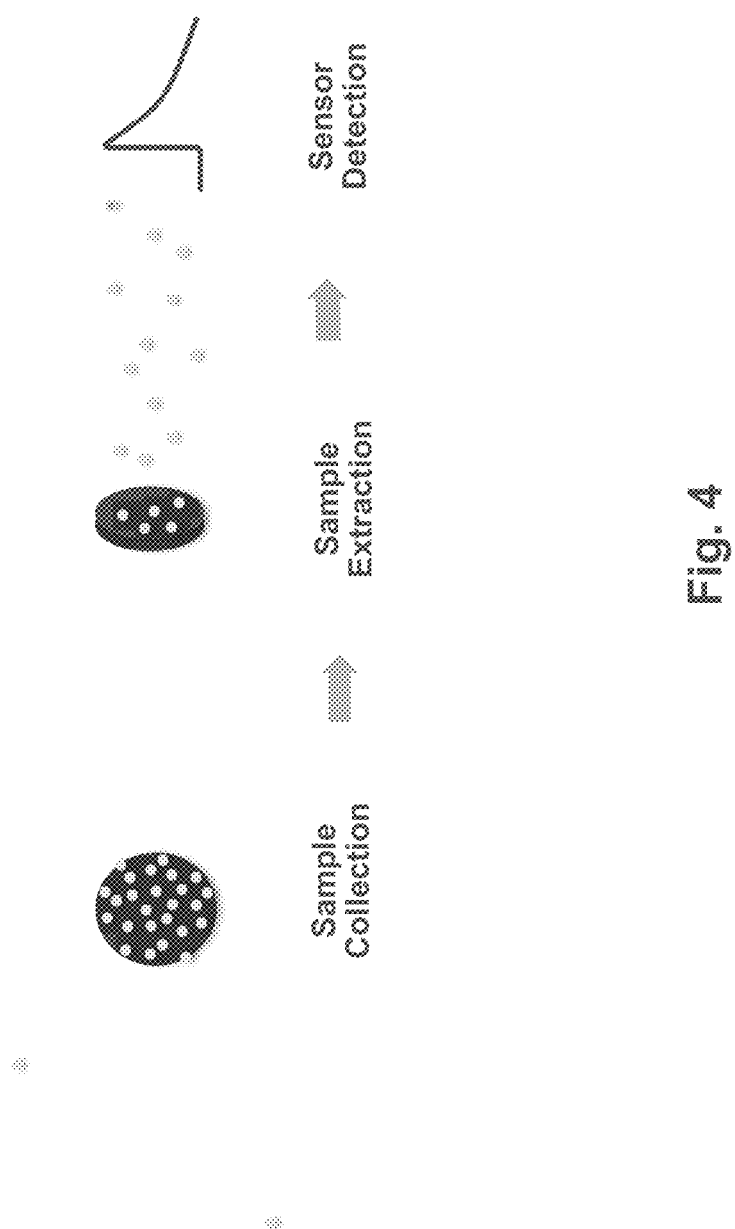
FIG. 4 is a diagrammatic representation of sample collection, sample extraction and sensor detection of volatile organic compounds using the area monitoring device.

In operation, the area monitoring device 20 is positioned at a desired location within a process plant, (or any other type of facility where VOCs or the like are to be monitored) ideally a location that is proximate to a large number of components that could potentially have VOCs leaking from them. With the area monitoring device 20 in its desired location, the passive sorbent material 22 constantly absorbs VOC molecules in ambient air at the location, as illustrated in FIG. 4. On a fixed schedule, such as, for example, once a week, the area monitoring device 20 is wirelessly activated by using the wireless transmitter 30 and the power and drive circuit 28. Upon activation, the gas sensor 26 is turned on and it undergoes a warm-up period in which the output of the gas sensor 26 gradually stabilizes. Once the gas sensor 26 establishes a stable baseline, the power and drive circuit 28 activates the heating element 24 by, for example, applying a preset voltage to the heating element 24. The heating element 24 is then heated up to a predefined temperature. Upon heating, the sorbent material 22 releases the VOC molecules as a gas to the surrounding air in a concentrated manner, as illustrated in FIG. 4. The gas sensor 26 senses the gas released by the sorbent material 22 and produces a change in its output, as illustrated in FIG. 4. The higher the VOC concentration in the released gas, the larger the change in the output of the gas sensor 26 is produced. The power to the heating element 24 remains on until the output of the gas sensor 26 returns to the baseline which will occur when the sorbent material 22 has released all of or substantially all of the VOC molecules therefrom. Data relating to the gas concentration sensed by the gas sensor 26 is then calculated by the power and drive circuit 28 based on the difference between a peak reading by the gas sensor 26 and the baseline reading by the gas sensor 26, or the integrated area of the recorded output (i.e. reading x time) over the entire heating period. This data is wirelessly transferred via the wireless transmitter 30 to a central control 42, and upon review/analysis, a determination can be made whether there are leaks that need to be addressed and, if such leaks are determined, further action can be taken to identify and repair the leak, thus potentially identifying and repairing leaks in advance of when/how they would be located via EPA Method 21 discussed herein.

Figure 5:
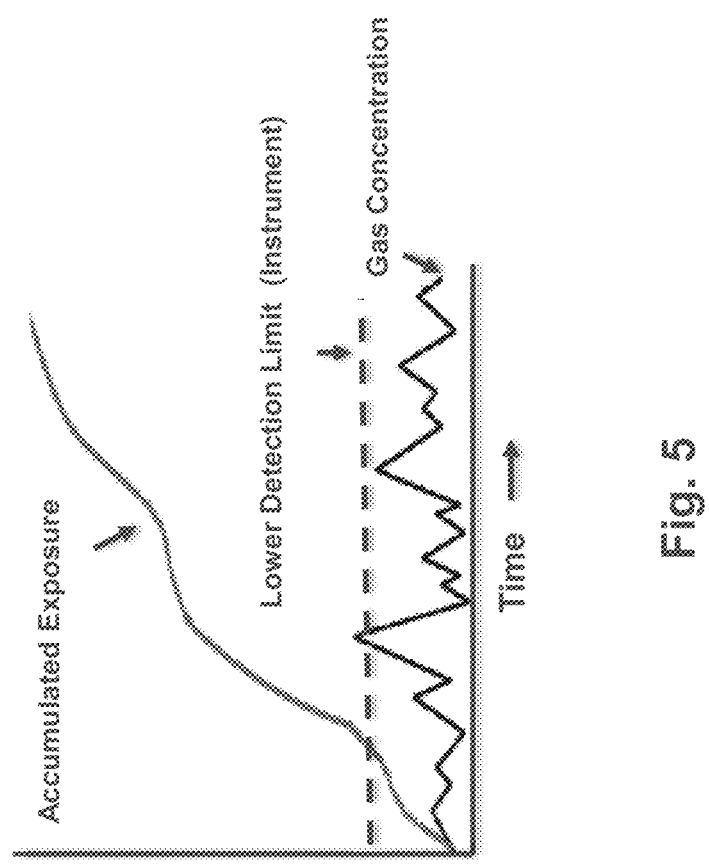
FIG. 5 is a graph showing a line providing an example of the gas concentration in the area over time, a line providing an example of accumulated gas over time, and a line showing the lower detection limit of a gas sensor of the area monitoring device.

A benefit of the area monitoring device 20 is that by accumulating the VOC molecules over time, an accumulated exposure is provided as shown in the graph in FIG. 5. The accumulated exposure is the total amount of gas absorbed represented by $$A = \int_0^T C(t)dt$$

where A is the total amount of gas absorbed, and T is the duration of the gas sampling time. The graph shown in FIG. 5 shows a line providing an example of the gas concentration in the area 34 over time, a line providing an example of accumulated gas over time, and a line showing the lower detection limit (LDL) of the gas sensor 26. If the gas sensor 26 was to be used without the sorbent material 22 and heating element 24 of the present area monitoring device 20, since gas concentration in air is typically extremely low, i.e. less than the LDL of the gas sensor 26, the gas sensor 26 alone may not detect the VOC molecules in the area 34 since the gas concentration is below the LDL. In addition, there may be moments that the gas concentration at the location will exceed the LDL of the gas sensor 26, but the gas sensor 26 may not be fast enough to respond to the gas due to constant change in wind velocity and/or wind direction at the location. Thus, the use of the gas sensor 26 without the sorbent material 22 and heating element 24 of the present area monitoring device 20 is undesirable.

The area monitoring device 20 of the first embodiment acts as a passive sampling device since the sorbent material 22 continues to accumulate VOC molecules over the fixed schedule without the use of power.

The power and drive circuit 28 includes a power supply 44, which may be a battery, which is used to power the gas sensor 26, the heating element 24 and the wireless transmitter 30, or may be main electric power. While a wireless transmitter 30 is disclosed, a wired transmitter can also be provided.

Figure 6:
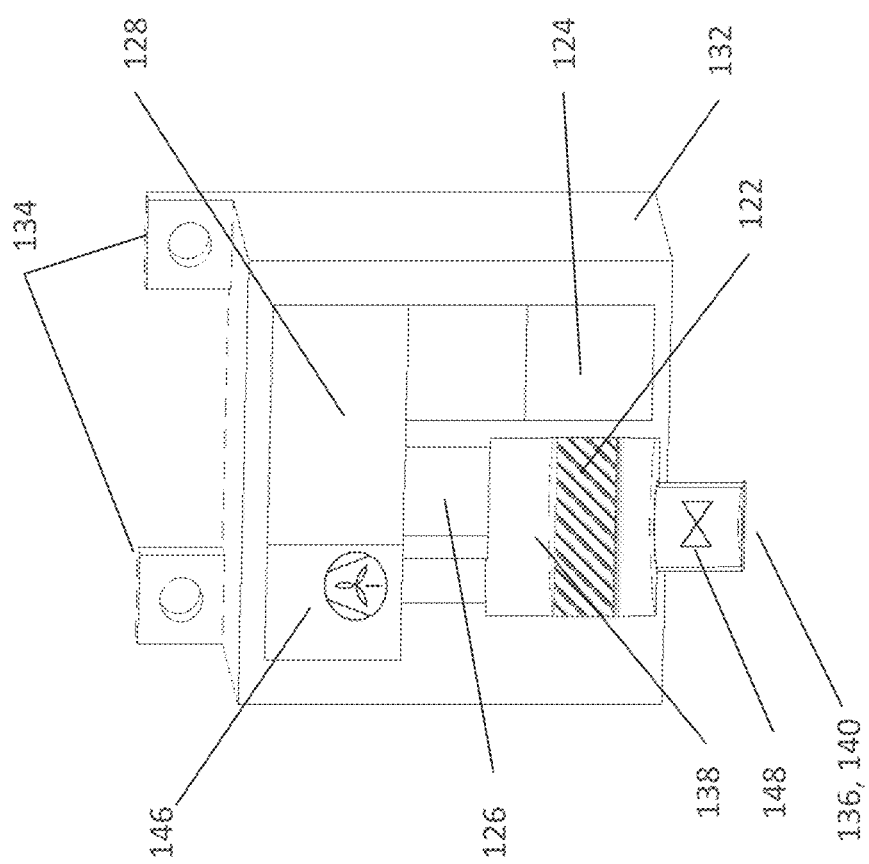
FIG. 6 is a cross-sectional view of an area monitoring device in a location in accordance with a second embodiment of the disclosure.
Figure 7:
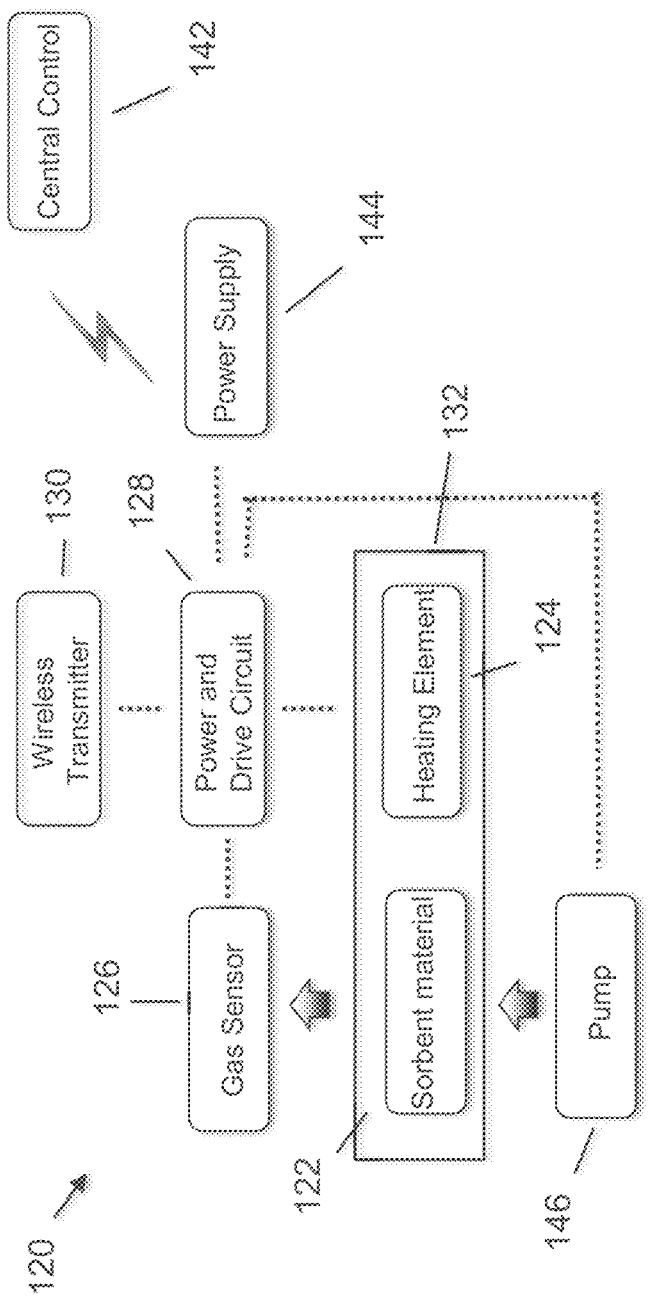
FIG. 7 is a schematic diagram of the area monitoring device of FIG. 6 and showing a central control.

A second embodiment of an area monitoring device 120 is illustrated in FIGS. 6 and 7. The area monitoring device 120 includes the components of the first embodiment of the area monitoring device 20, and further includes a pump 146 and an openable housing 132 such that the area monitoring device 120 acts as an active sampling device. The pump 146 is operatively connected to the power and drive circuit 128.

The housing 132 of the area monitoring device 120 may be a tube-like structure, or any other configured as desired. The area monitoring device 120 may be held in its desired position by any appropriate means 134, such as for example a bracket structure (as shown), such that it is suitably attached to a structure in the desired location where it is to monitor. The housing 132 may have an inlet 136 which opens to a chamber 138 within the housing 132 in which the sorbent material 122 and the heating element 124 are preferably seated. The housing 132 may be outfitted with a structure/device 148, such as a valve, that is operatively connected to the power and drive circuit 128 to allow ambient air at the location to pass into the chamber 138 within the housing 132 or to prevent such air from passing into the chamber 138.

The sorbent material 122 and the heating element 124 are within the chamber 138. The gas sensor 126, the power and drive circuit 128 and the wireless transmitter 130 may also be provided in the chamber 138 or may be separated from the housing 132. Normally, the housing 132 is closed such that the sorbent material 122 is not open to ambient air and therefore the sorbent material 122 is not collecting VOC molecules at the location. The housing 132 serves to protect the sorbent material 122 and the heating element 124 from the elements, and also to limit when the sorbent material 122 is exposed to the VOC molecules at the location.

When the power and drive circuit 128 is activated, the chamber 138 is opened and the pump 146 is turned on. The pump 146 either draws air samples to the sorbent material 122 through the chamber 138 of the housing 132 at a fixed air flow rate (as illustrated in FIG. 6) or pushes air samples to the sorbent material 122 through the chamber 138 of the housing 132 at a fixed air flow rate. After the pump 146 has been on for a predetermined period of time, the pump 146 is turned off and the gas sensor 126 and the heating element 124 can be turned on/activated in order to detect the concentration of VOC molecules using the gas sensor 126 as described above. The concentration of the VOC molecules can be calculated based on the total volume of the air sample it has passed through. The data from the gas sensor 126 is wirelessly transferred via the wireless transmitter 130 to the central control 140 and upon review/analysis, a determination can be made whether there are leaks that need to be addressed and, if such leaks are determined, further action can be taken to identify and repair the leak, thus potentially identifying and repairing leaks in advance of when/how they would be located via EPA Method 21 discussed herein.

The power and drive circuit 128 includes a power supply 144, which may be a battery, which is used to power the gas sensor 126, the heating element 124, the wireless transmitter 130 and the pump 146, or may be main electric power.

Active sampling using the pump 146 provides an advantage over passive sampling in that the results are less affected by wind because, depending on wind direction and speed, the sorbent material 122 can be exposed to different gas concentrations and air volumes. However, active sampling requires a pump 146 to operate which means higher power consumption. Furthermore, a mechanical pump 146 has a possibility of failure, especially under extreme weather conditions. Passive sampling consumes significantly less power and, in order to address the wind effect, hardware, and software solutions, for example a wind sensor assembly, may be employed.

The area monitoring device 20, 120 may be associated with a hood or other structure that will protect the area monitoring device 20, 120 from the weather, such as rain and wind, which weather conditions, depending on the configuration of the area monitoring device 20, 120, could potentially disrupt, or taint the information/results to be obtained from the area monitoring device 20, 120.

The use of the area monitoring device 20, 120 is an effective way of detecting extremely low concentrations of VOC molecules. The area monitoring device 20, 120 provides for detection of VOC molecules well below the detection limits of existing sensor technologies via a "pre-concentration" mechanism, while at the same time, automates sensor measurements by the gas sensor 26, 126 without human intervention. The sorbent material 22, 122 is regenerated every time sorbent material 22, 122 is heated, and therefore, the area monitoring device 20, 120 can operate in the field for many years without maintenance.

While particular embodiments are illustrated in and described with respect to the drawings, it is envisioned that those skilled in the art may devise various modifications without departing from the spirit and scope of the appended claims. It will therefore be appreciated that the scope of the disclosure and the appended claims is not limited to the specific embodiments illustrated in and discussed with respect to the drawings and that modifications and other embodiments are intended to be included within the scope of the disclosure and appended drawings. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure and the appended claims.

We claim:

1. A method of detecting leaks comprising the steps of:
(a) installing an area monitoring device in an area in which volatile organic compounds are emitted, the area monitoring device comprising a sorbent material, a heating element and a gas sensor;
(b) after the completion of step (a), allowing the sorbent material to continuously absorb volatile organic compound molecules in ambient air over an extended period of time of at least twenty-four hours;
(c) after the completion of step (b), heating the sorbent material using the heating element, thereby causing the sorbent material to release, in ambient air, a gas containing the volatile organic compound molecules that were absorbed in step (b), wherein the area monitoring device is not removed from the area during step (c);
(d) during and/or after the completion of step (c), sensing the volatile organic compound molecules released from the sorbent material, using the gas sensor in ambient air, wherein the area monitoring device is not removed from the area during the sensing; and
(e) after the completion of step (d), compiling data related to amounts of volatile organic compound molecules sensed by the gas sensor.

2. The method of claim 1, further comprising the step of:
(f) during and/or after the completion of step (e), transmitting the data to a location outside of the area.

3. The method of claim 1, wherein step (b) comprises allowing the sorbent material to continuously absorb volatile organic compound molecules in ambient air over an extended period of time of at least one week.

4. The method of claim 1, further comprising the steps of:
(f) prior to step (c) and after the completion of step (b), activating the gas sensor so that the gas sensor undergoes a warm-up period in which an output of the gas sensor stabilizes upon a baseline being established; and
(g) after the completion of step (d) and before or during step (e), deactivating the heating element when the output of the gas sensor returns to the baseline, and
wherein step (c) further comprises activating the heating element to heat the heating element to a predefined temperature, and
wherein step (d) further comprises detecting the volatile organic compound molecules that were released from the sorbent material to produce a change in the output of the gas sensor.

* * * * *